United States Patent [19]

Kadry

[11] Patent Number: 5,449,367
[45] Date of Patent: Sep. 12, 1995

[54] PRE-TIED KNOT FOR SURGICAL USE AND METHOD OF USING SAME

[76] Inventor: Othman Kadry, 263 Pine Ridge Dr., Bloomfield Hills, Mich. 48304

[21] Appl. No.: 101,433

[22] Filed: Aug. 2, 1993

[51] Int. Cl.$^6$ ............................................. A61B 17/00
[52] U.S. Cl. .................................. 606/148; 606/139; 289/1.2; 289/18.1
[58] Field of Search ............... 606/139, 148, 205, 206, 606/207, 144; 289/1.2, 18.1

[56] References Cited

U.S. PATENT DOCUMENTS

| | | | |
|---|---|---|---|
| 879,758 | 6/1907 | Foster . | |
| 1,757,129 | 6/1930 | McClure . | |
| 3,580,256 | 5/1971 | Wilkinson . | |
| 4,760,848 | 8/1988 | Hasson | 606/206 |
| 5,037,433 | 8/1991 | Wilk et al. | 606/139 |
| 5,284,485 | 2/1994 | Kammerer et al. | 606/148 |

OTHER PUBLICATIONS

Graumont and Hensel, *Encyclopedia of Knots & Fancy Ropework*, Cornell Maritime Press, New York 1945, pp. Preface, 12, 13, 15, 18, 20, 21.

*Primary Examiner*—Stephen C. Pellegrino
*Assistant Examiner*—Jeffrey A. Schmidt
*Attorney, Agent, or Firm*—Weintraub, DuRoss & Brady

[57] ABSTRACT

A pre-tied suturing knot for use with a surgical needle for endoscopic procedures and the method for making and using the pre-tied knot for tying the suture in situ. The pre-tied knot is tied from suturing thread and surrounds the shaft of a needle holder or grasper. A needle holder is placed on the U-shaped loop and the U-shaped loop or bight is pulled back upon itself to create a first loop, a second loop and two loopholes. The distal end of the suture thread is threaded over the proximal end and through the loopholes creating the nascent knot. The pre-tied knot is utilized after the tissue has been pierced with the needle. Thereafter, the needle holder is withdrawn from the suturing site, thereby pulling the suture thread against and through the tissue edges and moving the pre-tied knot along the shaft of the needle holder over the clamp and into position near the suturing site. A method for using the pre-tied knot wherein the proximal end of the suturing thread which can have the needle is drawn away from the suturing site thereby emplacing the knot at the suturing site. The knot itself has loops with bights interconnecting the loops and forming loopholes inside the loops.

4 Claims, 2 Drawing Sheets

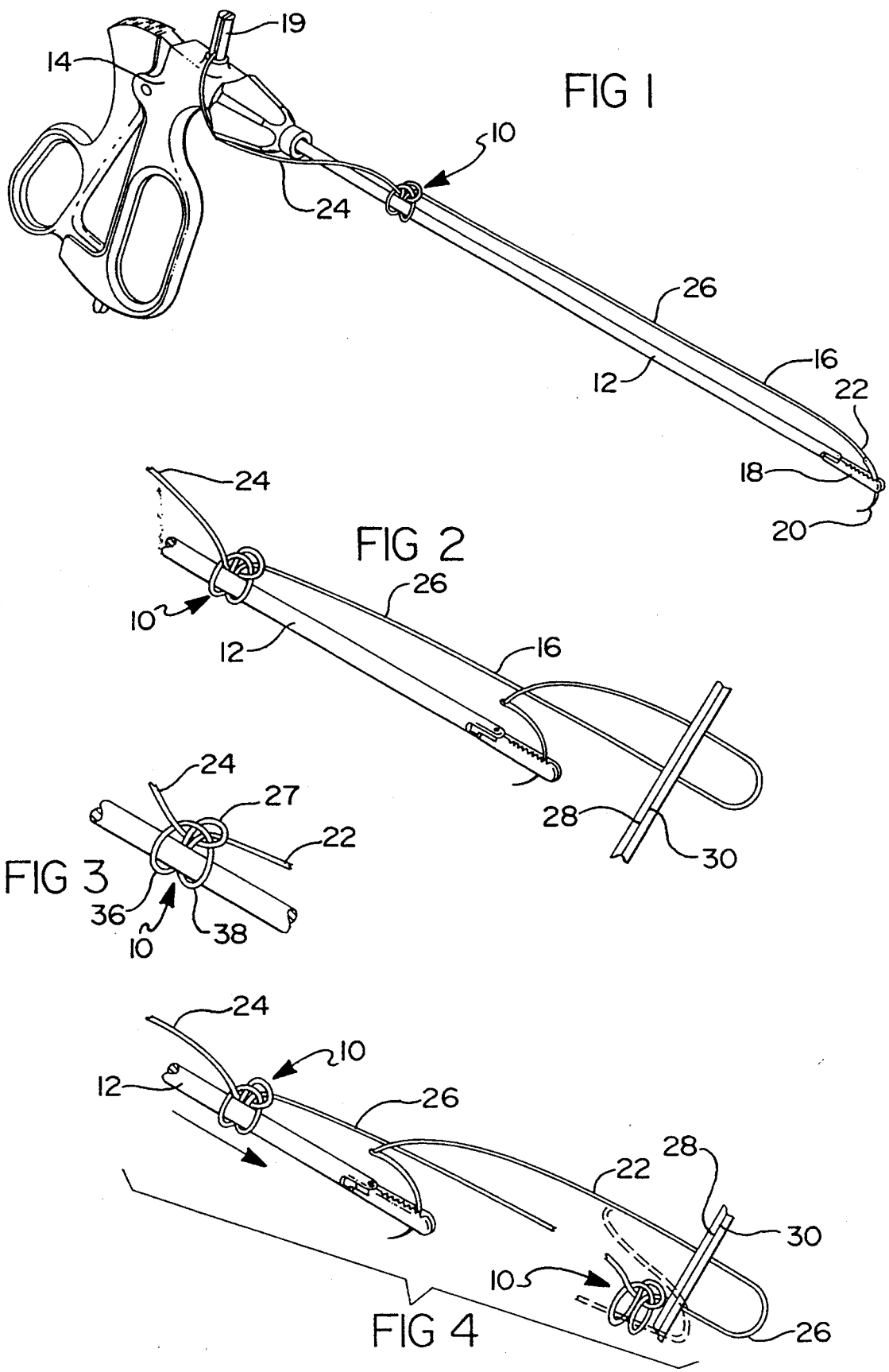

PRE-TIED KNOT FOR SURGICAL USE AND METHOD OF USING SAME

BACKGROUND OF THE INVENTION

I. Field of the Invention

The present invention relates to knots for surgical use. More particularly, the present invention relates to a pre-tied suturing knot and holder therefor. Even more particularly, the present invention concerns a knot for use with a surgical needle holder or grasping instrument for combined extrocorporeal and intracorporeal endoscopic surgical procedures and a method for using same.

II. Description of the Relevant Art

After a surgical procedure is performed or when an open injury occurs, tissues must be stitched or sutured to allow the incision or wound to heal, be it either an internal or external procedure. Suturing, that is, the typing of a thread knot at the incision site, is well-known in the art. Moreover, pre-tied sutures and methods of suturing for external surgical use likewise are known, such as is described in U.S. Pat. No. 3,580,256 to Wilkinson et alia. The Wilkinson et alia patent describes a pre-tied suture that is encased in a see-through material, taking the form of a thin, flat wafer. In use, the surgeon stitches the tissue together and then directs the needle through the loops in the wafer and draws it tight in order to make the knot. Clearly, such a convention could not be used for endoscopic and other internal surgical techniques.

In contrast, internal surgery, such as endoscopic surgery, is performed within the interior of a body cavity or hollow organ with the help of an endoscope or similar device to visualize the interior portions of the body where the surgery is to be performed. Miniaturized instruments are utilized to incise and subsequently suture the incision. The surgeon observes the surgical procedures through a visual device whose output is displayed on a video monitor.

In order to perform the suturing in the interior of the body, a curved needle with a fine suturing thread is held with a gun-shaped needle holder or grasper. The needle holder includes a clamp to securely hold the needle. The clamp can be rotated through 360° for maneuvering the needle to perform the desired stitching. The drawbacks of endoscopic and similar surgery are both the distance the suturing site is located inside the body as well as the limited space available within the body for manipulation of the surgical instruments themselves as used for the suturing process. With respect to the latter, a problem arises in manipulating the curved needle for easily tying a knot for closing the surgical incision in situ. Many manipulations of the needle, needle holder and suture thread are required for each suturing knot that is placed at the incision site.

Likewise, the same manipulative problems are encountered in trying to limit blood flow, in tourniquet-fashion, of from blood vessels which are termed "bleeders".

Thus, it is to be appreciated that a pre-tied suture, employable with a needle clamp or grasping instrument, could greatly facilitate endoscopic and other internal body surgical procedures. It is to this to which the present invention is directed.

SUMMARY OF THE PRESENT INVENTION

The present invention in a first aspect provides a pre-tied surgical knot which can be slidably mounted onto a needle holder or grasping instrument, the knot comprising:

a suturing thread having a distal end, a proximal end and a medial or bight portion;

the thread being formed into a U-shaped loop, the U-shaped loop adapted to be wrapped around the needle holder or grasping instrument to define a first loop and a second loop spaced from the first loop;

a medial portion of the distal end and a medial portion of the proximal end being partially drawn into a space defined between the bight and the needle holder to provide a pair of loopholes between the bight and the first loop and the second loop;

the distal end of the thread being threaded through the loophole to form the knot;

the thread being drawn through tissue edges to suture the tissue edges; and the needle holder being withdrawn from the tissue edges, drawing the knot down the needle holder and over the clamp and off the needle holder into position at the tissue edges.

The present invention further provides a combined pre-tied suturing knot and a needle holder or grasping instrument, comprising:

the suture having a distal end, a proximal end and a medial portion, the proximal end of the suture terminating at and secured to a needle, adapted to be clamped to the needle holder;

the suture surrounding the needle holder being formed into the knot, defined hereinabove, and where the loopholes slidingly surround the shaft of the needle holder.

In use, a needle is placed through the tissue edges, then the needle holder is withdrawn, moving the knot off the shaft and to the sutured tissue site.

Thus, the present invention also defines a method for using the pre-tied suturing knot comprising:

forming the above-defined knot in a suture surrounding a first needle holder;

manipulating the needle to join tissue edges;

pulling the needle holder away from the suturing site to draw the knot off the needle holder into proximity of the suturing site to secure the tissue edges together.

The invention, preferably, is employed for endoscopic surgical and other internal stitching procedures.

For a more complete understanding of the present invention, reference is made to the following detailed description to be read in conjunction with the accompanying drawing, in which.

A BRIEF DESCRIPTION OF THE DRAWINGS

FIG. 1 is an environmental view of a pre-tied suturing knot surrounding the shaft of a needle holder in accordance with the present invention;

FIG. 2 is a perspective view of a needle after suturing;

FIG. 3 is a perspective view of the pre-tied knot hereof;

FIG. 4 is a broken perspective view of the pre-tied knot on the needle holder and showing the pre-tied knot in position on one side of tissue that has been joined.

DETAILED DESCRIPTION OF THE PREFERRED EMBODIMENT

Figure 5A:
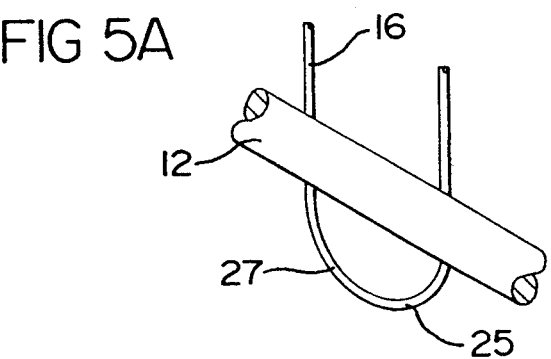
FIGS. 5A, 5B, 5C and 5D are step by step front views depicting formation of the knot being formed.

At the outset, it is to be noted that the present invention as described herein is directed to a pre-tied suturing knot for endoscopic surgical procedures and a method of use therefor. However, it is to be understood that the present invention may also be used in conjunction with other surgical procedures, specifically, internal body suturing. The knot of the invention can be either intracorporeal or extracorporeal.

Likewise, the present invention can be used to tie off, in tourniquet fashion, a "bleeder". Also, although the present invention is described with respect to needle holders, it is to be understood that it is equally applicable to or grasping instruments.

It is also to be understood that the suture thread could be detached from the needle or used independently from the needle.

Referring now to the drawing, a preferred embodiment of the present invention is shown in FIG. 1, to wit, a pre-tied knot 10 surrounding the shaft 12 of a first needle holder or grasping instrument 14. The pre-tied knot 10 can be tied on any tube-shaped device or even a digit of the hand of the surgeon if that is more expedient for the suturing. Typically, where used for endoscopic surgery, the first needle holder 14 is manipulated from outside the body of the patient and is observed through visual display media well-known to the skilled artisan. The grasping instrument 14, per se, is well-known and commercially available, such as those sold by Ethicon and Auto Suture. Likewise, needle holders such as those sold by Cook, Inc. and Stortz Medical may be used.

In practicing the present invention, a length of suture thread 16 is used to form a knot 10. As shown, the suture thread 16 terminates at a curved surgical needle 20 attached at the proximal end 22 of the thread 16.

The suture thread 16 has a distal end 24 away from the needle 20 and a medial portion 26 therebetween. The suture thread 16 is removably and slidably tied around the shaft 12 of the first needle holder 14 in the configuration of the knot 10.

As shown, the curved needle 20 is clamped in a clamp 18 at the terminus of the shaft 12 of the first needle holder 14. The opposed end of the first needle holder 14 has means 19 for grasping to facilitate the use thereof.

As shown in FIG. 2, the knot 10 is tied on the shaft 12. Then, the curved needle 20 at the proximal end 22 of the suture thread 16 is grasped by the first needle holder 14 or any grasping instrument. Thereafter, the curved needle 20 is used to join edges of body tissues 28, 30 together in a well-known manner. The curved needle 20 is manipulated through the tissue edges 28, 30 to draw the suture thread 16 therethrough. Then the first needle holder 14 is pulled away from the suturing site and the knot 10 is pulled over the clamp 18 and off the shaft 12.

In performance of this action of suturing, the first needle holder 14 is moved away from the suturing site towards the exterior of the body cavity or hollow organ (not shown). The suture thread 16 pulls against the tissue edges 28, 30 and causes the knot 10 to ride down the shaft 12 and over the clamp 18 into position at the suturing site. Thus, the knot 10 is moved along the shaft 12 of the first needle holder 14, directed over the clamp 18 and over the curved needle 20 or, if the curved needle 20 is detached, over the proximal end 22 of the suture thread 16 and off the first needle holder 14 into position near the suturing site, as is best shown with phantom lines in FIG. 4.

Consequently, the knot 10 is securely tied without awkward and unnecessary extraneous internal manipulation of the curved needle 20 and suture thread 16. This placement of the knot 10 holds the tissue edges 28, 30 together.

The pre-tied knot 10 hereof is best shown in FIG. 3 and in a slightly loosened configuration. The knot 10 generally is created by forming the suture thread 16 into a U-shaped loop 25, having the distal end 24, the proximal end 22 and a bight section 27, and placing a shaft 12 of the needle holder 14 on the U-shaped loop 25. The bight 27 of the U-shaped loop 25 is then folded upon itself between the ends 22, 24, and around the shaft 12 causing formation of loops 36 and 38, respectively, as shown. The medial portion 26 of the distal end 24 and proximal end 22 is then drawn partially into the space between the loops 36, 38 and below the bight 27 to form loopholes 29, 31, respectively. The distal end 24 of the suture thread 16 is then wrapped around the proximal end 22, and, then, laced through the loopholes 29, 31 as shown.

Figure 5B:
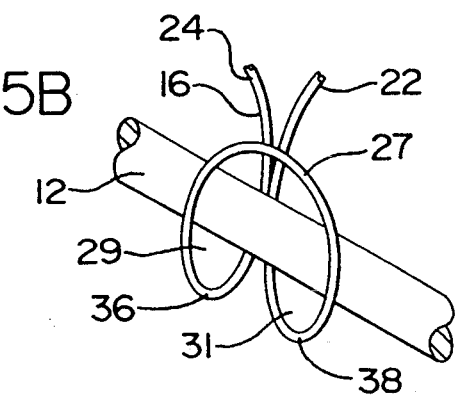
Figure 5C:
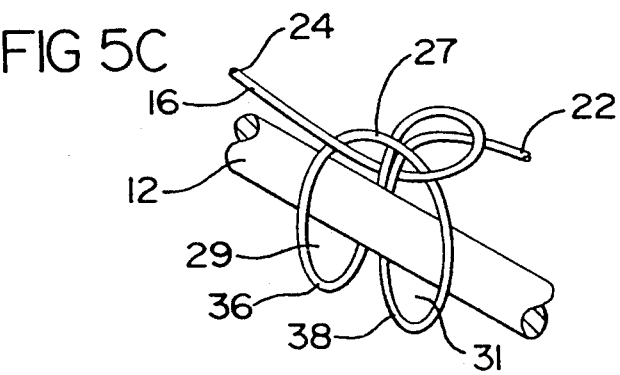
Figure 5D:
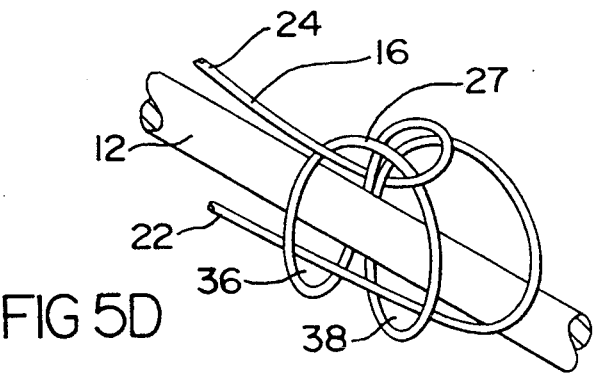

The preferred steps in forming the knot 10 are shown in greater detail in FIGS. 5A, 5B, 5C and 5D. As shown, the U-shaped loop 25 of suture thread 16 is formed as shown in FIG. 5A. The shaft 12 of the needle holder 14 is placed across the U-shaped loop 25. Subsequently, the U-shaped loop 25 is brought up on itself by grasping the ends 24 and 22 together, bringing the ends 24 and 22 in front of the bight 27, forming the two loops 36, 38 as seen in FIG. 5B. Two loopholes 29, 31 are respectively formed inside the two loops 36, 38. Then the distal end 24 of the thread 16 is brought over or in front of the proximal end 22 of the thread 16 and laced or threaded through the loopholes 29, 31 behind the distal end 24 and proximal end 22 as shown, to create the knot 10. After the tissue edges 28, 30 (not shown in this figure) are stitched together, the curved needle 20 at the proximal end 22 of the suture thread 16 or the proximal end 22 itself if the needle 20 is detached, is drawn back on itself and is also drawn through loopholes 36, 38 by pulling the needle holder (not shown) away from the suturing site to form the knot 10, as shown in FIG. 5D. This pulling away of the needle holder tightens and completes the knot 10 and moves the knot 10 off the shaft 12 over the clamp 18 (not shown) and into proximity of the suturing site, as hereinabove described.

It is to be understood that the shaft 12 of the needle holder 14 extends through the knot 10 but the knot 10 can be formed without using the needle holder 14. A digit of the hand of the surgeon hand can be advantageously employed for forming the knot of the invention.

As noted, the present knot can be used in tourniquet fashion for a bleeder or the like, by wrapping the thread around the vessel and drawing the knot off the shaft in the manner heretofore described.

As can be seen from the preceding description it can be seen that a pre-tied suturing knot which greatly facilities the stitching of internal tissues.

Having thus described the present invention, what is claimed is:

4. In a suturing knot of the type configured to be pre-tied, in a length of suture thread having a distal end and a proximal end for securing to a suturing needle, and slidably mounted on a shaft, the improvement comprising:

first, second, and central bight portions between the proximal and distal ends, the first bight portion is adjacent both the center bight portion and a medial portion of the distal end, the second bight portion is adjacent both the center bight portion and a medial portion of the proximal end, the medial portion of each end being disposed in contact with the center bight portion to define a pair of spaced apart loopholes, wherein the periphery of the first loophole is defined by the medial portion of the distal end, the first bight portion and the center bight portion, and the periphery of the second loophole is defined by the medial portion of the proximal end, the second bight portion and the center bight portion, the distal end wound over the medial portion of the proximal end but outside of the second loophole, extending over the center bight and through the second loophole in a first direction, back around behind both the proximal and distal medial portions, through the first loophole in a second direction, opposite of the first direction, wherein the loopholes are configured to receive a shaft therethrough.

1. In combination, a surgical needle holder and a pre-tied suturing knot comprising:

(a) a pre-tied suture knot formed in a suture thread having a distal end, and a proximal end for securing to a suturing needle, wherein the knot is characterized by:

first, second, and central bight portions between the proximal and distal ends, the first bight portion is adjacent both the center bight portion and a medial portion of the distal end, the second bight portion is adjacent both the center bight portion and a medial portion of the proximal end, the medial portion of each end being disposed in contact with the center bight portion to define a pair of spaced apart loopholes, wherein the periphery of the first loophole is defined by the medial portion of the distal end, the first bight portion and the center bight portion, and the periphery of the second loophole is defined by the medial portion of the proximal end, the second bight portion and the center bight portion, the distal end wound over the medial portion of the proximal end but outside of the second loophole, extending over the center bight and through the second loophole in a first direction, back around behind both the proximal and distal medial portions, through the first loophole in a second direction, opposite of the first direction, and (b) a needle holder having a shaft which slidably mounts the suture knot, wherein the shaft extends in the first direction through both the first and second loopholes.

2. The combination of claim 1, which further comprises:

(a) a needle secured to the proximal end of the suture.

3. A method for suturing internal body cavity tissues, employing a pre-tied suturing knot, comprising:

(a) suturing a site with the combination of claim 2;

(b) drawing the proximal end of the thread through the pair of spaced apart loops to slip the knot off the needle holder at the suturing site to secure the tissues together.

* * * * *